United States Patent [19]

Hassel et al.

[11] Patent Number: 4,811,742

[45] Date of Patent: Mar. 14, 1989

[54] PROPORTIONAL RESPONSE ELECTRICAL MUSCLE STIMULATION

[75] Inventors: William Hassel, Ft. Lauderdale; William Mee, Pompano Beach, both of Fla.

[73] Assignee: Verimed, Inc., Ft. Lauderdale, Fla.

[21] Appl. No.: 743,635

[22] Filed: Jun. 11, 1985

[51] Int. Cl.$^4$ ............................................. A61B 5/04
[52] U.S. Cl. ................................... 128/733; 128/905; 128/741
[58] Field of Search ............................. 128/731-733, 128/905, 774, 782, 741

[56] References Cited

U.S. PATENT DOCUMENTS

| | | | |
|---|---|---|---|
| 3,641,993 | 2/1972 | Gaarder et al. | 128/733 |
| 3,905,355 | 9/1975 | Brudny | 128/733 |
| 4,031,883 | 6/1977 | Fehmi et al. | 128/733 X |
| 4,170,225 | 10/1979 | Criglar et al. | 128/733 |
| 4,291,705 | 9/1981 | Severinghaus et al. | 128/741 X |
| 4,305,402 | 12/1981 | Katims | 128/732 X |
| 4,474,186 | 10/1984 | Ledley et al. | 128/733 |
| 4,492,233 | 1/1985 | Petrofsky et al. | 128/905 X |
| 4,595,018 | 6/1986 | Rantala | 128/733 |
| 4,619,266 | 10/1986 | Hodgson | 128/733 X |
| 4,690,142 | 9/1987 | Ross et al. | 128/733 X |

FOREIGN PATENT DOCUMENTS

| | | | |
|---|---|---|---|
| 2457854 | 6/1975 | Fed. Rep. of Germany | 128/733 |
| 0129157 | 1/1978 | Fed. Rep. of Germany | 128/733 |

OTHER PUBLICATIONS

Othotic Systems Using Functional Electrical Stimulation and Myeolectric Control, S. Rebersek et al, Final Report Project No. 19-P-58391-F-01, pp. 58-71.

Primary Examiner—Edward M. Coven
Assistant Examiner—Angela D. Sykes
Attorney, Agent, or Firm—Lowe, Price, LeBlanc, Becker & Shur

[57] ABSTRACT

Excitation of the skeletal musculature of a subject is measured by an electromyogram (EMG), processed and applied to control application to the musculature of electrical muscle stimulation (EMS) signals proportional to the electrical nerve impulses. The invention is useful for re-education and/or amplification of muscular control where motor control has suffered impairment.

16 Claims, 4 Drawing Sheets

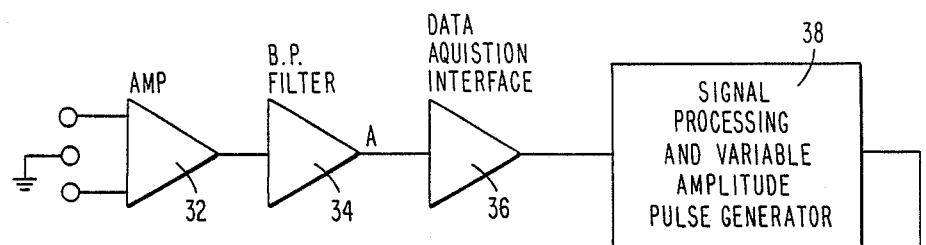
Fig. 3
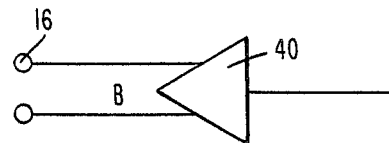
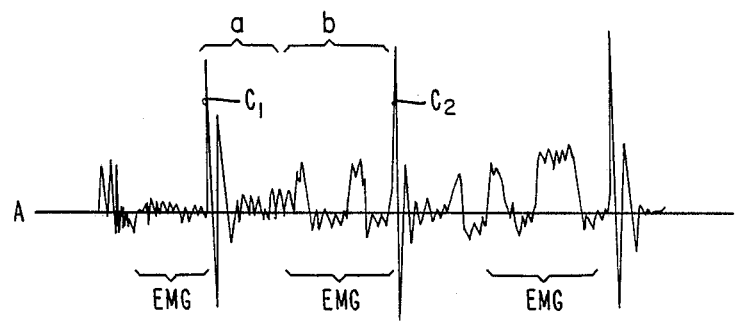
Fig. 4A
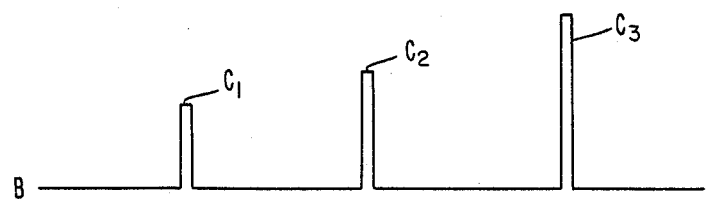
Fig. 4B (A) EMG & STIMULUS ARTIFACT (B) EMG ENVELOPE & STIMULUS ARTIFACT (C) DATA AQUISITION ENABLE (D) PROPORTIONAL OUTPUT EMS

PROPORTIONAL RESPONSE ELECTRICAL MUSCLE STIMULATION

TECHNICAL FIELD

The invention relates generally to electrical stimulation of muscles in rehabilitation therapy, and more particularly, toward neuromuscular re-education by electrical stimulation of muscles in response to EMG measurements.

BACKGROUND ART

In muscular contraction, electrical nerve impulses or action potentials are conducted along nerve pathways to muscle fibers at the myoneural junction. Muscle fibers, thus excited, contract as the action potential instantaneously propagates along the fibers. For a single muscle fiber, this event is known as a motor unit action potential. In muscular contraction, gross muscular tension is effected by a series of excitations through many muscle fibers.

When many muscle fibers contract simultaneously, the total electrical potential arising from the conductive summation of individual motor unit action potentials measured at the skin is great enough to be electronically measured with an electromyogram (EMG). Instantaneous EMG measurement is accomplished by attaching surface electrodes to the skin or inserting needle electrodes into the muscle and recording the instantaneous changes in the magnitude of the raw myographic signal. In integrated EMG measurement (IEMG), the raw signal is integrated, or time averaged, over a short period of time and then recorded.

This latter method is preferential in sensory feedback motor training, wherein the overall magnitude of the myographic response is of primary importance. Changes in the level of response by a conscious effort to contract or relax muscle groups on the part of the subject is "fed back" to the subject in the form of sensory stimuli. Invariably, the stimulus is either auditory, visual or a combination of the two, and its strength usually is proportional to the level of motor activity. Thus, where the pathways of neuromuscular communication and control are weak, damaged, decerebrate, untrained or lacking in proprioceptive effect, the feedback stimulus provides a singular method for bringing muscular coordination into the arena of conscious awareness and control. While the mechanisms of sensory feedback are not as yet precisely known, the technique is found to produce positive results in many areas of clinical, physical, sports and behavioral medicine.

Electrical stimulation of excitable nerve and muscle tissue is an important therapeutic modality applicable to the clinical treatment of neuromuscular and muscoloskeletal problems wherein the tension of skelatal musculature is affected through gross elicitation of motor unit contraction by an externally applied electrical current. Electrical muscle stimulation (EMS) devices typically employ time varying waveforms which are applied to specific surface sites on muscle groups. Clinical application of electrical stimulation includes facilitation of voluntary motor function, muscle strength enhancement, motion range improvement and spasticity inhibition. Reference is made to Benton et al, "Functional Electrical Stimulation—A Practical Clinical Guide", Second Edition, Ranchos Los Amigos Rehabilitation Engineering Center, Downey, Calif., pages 31–52.

It is thus clear that sensory feedback and EMS share many of the same patient populations and treatment objectives. Patients suffering central nervous system insult, either from head trauma or stroke, and spinal injury patients having incomplete damage to the spinal cord and orthopedic patients, may be treated by rehabilitation programs involving EMS and sensory feedback administered separately.

Recently, work has been undertaken to combine EMS and EMG technology to produce bioelectrically controlled electrical stimulators incorporating a feedback system to provide information on the correspondence between a preset program of movements and motions actually performed by a subject. In U.S. application Ser. No. 697,897, filed on Feb. 4, 1985 now abandoned and assigned to the assignee of this invention, EMG measurements made near the muscles to be electrically stimulated are compared with an EMG signal threshold level corresponding to a programmed therapeutic goal. When the measured EMG signal meets or exceeds this EMG threshold level, electrical muscle stimulation is applied to the muscle site, to effect kinesthetic movement of the muscle group from which the EMG signal is being measured. EMS stimulation is, however, applied with a "zero-bang" control strategy, that is, once the stimulation cycle has been voluntarily activated on the part of the subject, by virtue of the EMG magnitude, motor activation is realized purely as a function of the preprogrammed EMS cycle, rather than volitional control. However, we now believe that significant improvements in neuromuscular re-education can be realized by volitional control electrical muscle stimulation, not provided heretofore. We further believe that application of volitional control electrical muscle stimulation incorporating the technologies of EMG and EMS therapy in a unique manner may produce syneristic and accelerated therapeutic benefits to the neurologically compromised subject beyond those of traditional EMG and EMS treatment. This is in contrast with the current clinical use of EMS wherein control of muscles by electrical stimulation is passive, i.e., not controlled as a function of neurological signals developed by the subject.

It is accordingly an object of the invention to provide a method and system for improved neuromuscular reeducation.

It is a more specific object to provide a method of and system for volitional control electrical muscle stimulation, i.e., muscle stimulation by an electrical signal that is a predetermined, preferably linear, function of the IEMG signal.

During our experimentation with a human subject undergoing neuromuscular rehabilitation therapy involving application of EMS signals to a muscle site and making EMG measurements in close proximity to or specifically at that site, the EMG measurement tends to become obscured by an EMG artifact that follows each EMS pulse applied to the muscle. In those experiments, we have found that the EMG signal in fact becomes unusable as a therapeutic parameter at high levels of EMS, particularly when EMG and EMS take place at a common site. It is accordingly an additional object of the invention to provide a system for "masking" obscuration of the raw EMG signal by EMS pulses applied to the muscles in therapy involving volitional control electrical muscle stimulation.

DISCLOSURE OF THE INVENTION

Muscular re-education by electrical stimulation, in accordance with the invention, comprises measuring electromyographic (EMG) signals developed by muscles to be stimulated, processing the measured signals to obtain a measurement of the overall EMG signal magnitude and applying to the muscles an electrical muscle stimulation (EMS) signal whose amplitude is linearly or monotonically or otherwise related to the magnitude of the processed EMG signal. In accordance with a preferred embodiment, the EMG signal is amplified, filtered and translated to a stimulus magnitude, while the residual pulse artifact is suppressed by time multiplexing and analog filtration.

An apparatus for carrying out the invention comprises first electrodes to be applied to the skin of a patient near muscles to be stimulated, and first means coupled to the first electrodes for generating EMS signals. Second electrodes are applied to the skin in proximity to the first electrodes for making EMG measurements, and second means coupled to the second electrodes produce EMG measurement signals. A processor means responsive to the second means controls the first means to generate EMS signals proportional to the EMG measurement signals.

In accordance with another aspect of the invention, the EMG signals are sampled following decay of EMG artifacts caused by the applied EMS signals, to avoid distortion or obscuration of the EMG measurements. The raw EMG signals are applied to an envelope detector to obtain an EMG envelope that is further processed and applied to control the magnitude of EMS pulses supplied to the first electrodes.

Preferably, the second electrodes are positioned on the skin of the subject outside a primary stimulation current path of the EMS signal produced by the first electrodes, to reduce the contribution of EMS pulse artifact.

The invention thus provides electrical stimulation of muscles in an amount proportional to the EMG produced by the subject undergoing therapy. It is, in fact, contemplated that the first and second electrodes as well as the processor may be subcutaneously implanted in the subject for permanent in vivo operation as a neuromuscular "amplifier". In either subcutaneous or supercutaneous realizations the instrument has potential as a prosthetic device. It is thus an additional object of the invention to provide a prosthetic method of and system for neuromuscular amplification by electrical stimulation of muscles in proportion to measured EMG biofeedback.

Still other objects and advantages of the present invention will become readily apparent to those skilled in this art from the following detailed description, wherein we have shown and described only the preferred embodiments of the invention, simply by way of illustration of the best modes contemplated by us of carrying out our invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

FIG. 3 is a simplified schematic diagram of a circuit for generating proportional response electrical muscle stimulation signals, in accordance with the invention;

FIG. 4A is a diagram of a waveform showing a raw EMG in the presence of periodic EMS signals;

FIG. 4B is a diagram of proportional EMS signals developed by the circuit of FIG. 3;

FIG. 5 is a more detailed schematic diagram of a circuit for generating proportional response EMS signals in accordance with the invention.

BEST MODE FOR PRACTICING THE INVENTION

Figure 1:
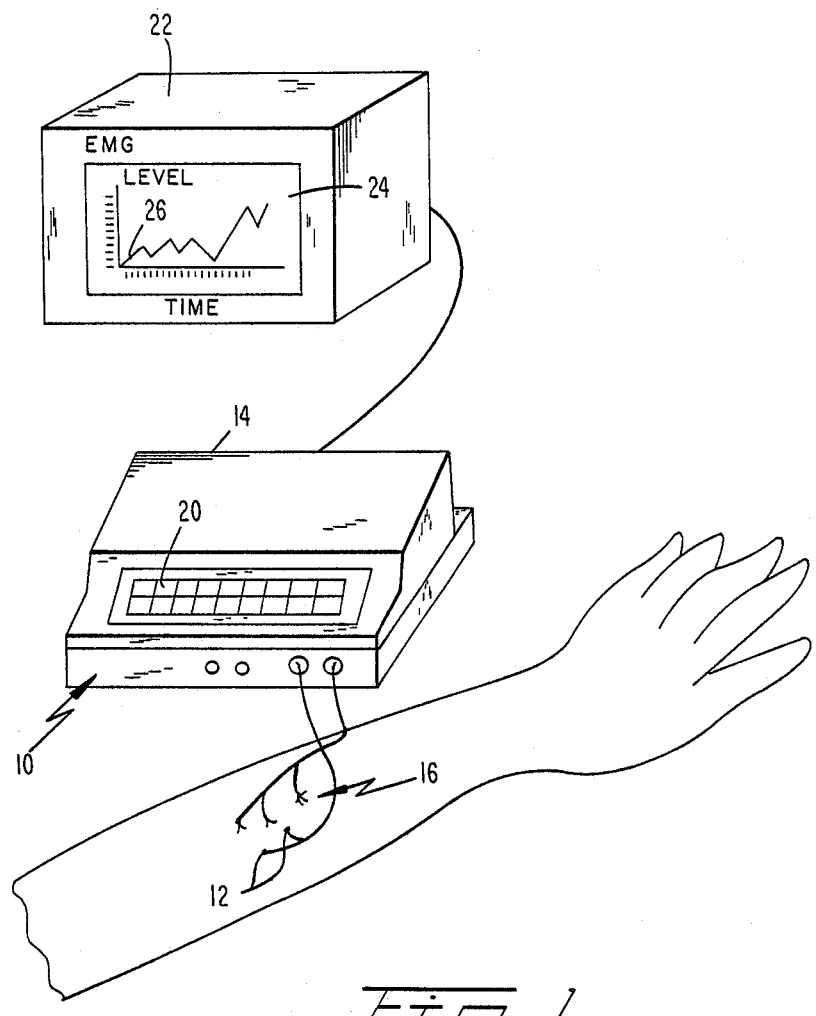
FIG. 1 is a diagram of a neuromuscular re-education system in accordance with the invention, connected to the arm of a subject.

Referring to FIG. 1, the EMG and EMS processing unit 10 is wired to a pair of transcutaneous electrodes 12 to be applied to an appropriate muscle group of a limb of a subject. Electrode types and placement, as well as electrical stimulation waveforms to be applied to muscle groups in muscle rehabilitation therapy, are described in detail in "Functional Electrical Stimulation—A Practical Clinical Guide", supra. Predetermined stimulus pulse rate, pulse width and waveform type are provided by circuitry within the processing unit 10. A set of EMG electrodes 16 detect EMG from enervated musculature, to be applied over lines 18 to one input of console 14. The EMG electrodes 16 are of a type and are positioned on the skin in a manner also discussed in detail in "Functional Electrical Stimulation—A Practical Guide", supra.

A monitor 22, which preferably includes a cathode ray tube (CRT) 24, is controlled by circuitry in console 14 to display the measured EMG signal to the subject as well as to attending personnel, visual feedback during the therapeutic session. The console keyboard 20 enables the clinician/operator to select parameters influencing the processing of the EMG and stimulus waveforms in processor 10 as well as auditory and visual feedback via the console 22 by virtue of displayed selection "menus" on the CRT 24 prior to initiating a therapeutic session.

In accordance with a principal object of the invention, circuitry within the processor 10 processes the EMG signals detected by electrodes 16 and, in response, controls the muscle stimulus waveform amplitude applied to the subject at electrodes 12. The relationship between processed EMG and applied EMS signals preferably is linear, although other functional relationships, such as logarithmic, etc., including negative or inverse relations, can also be programmed.

Figures 6A, 6B, 6C, 6D:
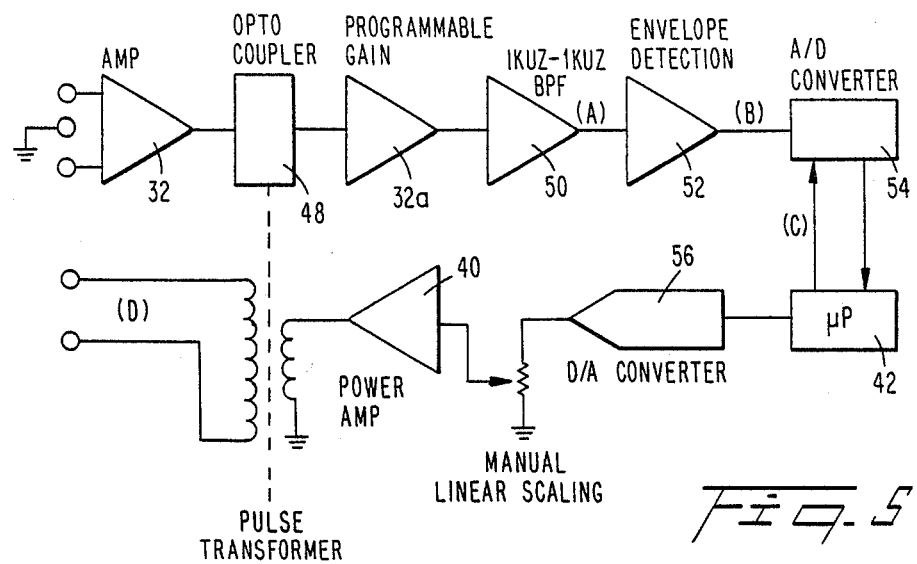
FIGS. 6A-6D are diagrams of waveforms developed by the circuit of FIG. 5.

The placement of electrodes 12 and 16 on the skin of the subject is not arbitrary. In addition to the general factors affecting electrode placement described in the Benton publication, supra, and elsewhere, we have determined from experimentation that the EMG electrodes 16 preferably are located on the skin of the subject outside a primary stimulation current path produced in the skin by EMS electrodes 12. Thus, the orientation of electrodes shown in FIG. 2A, with EMG electrodes 16 positioned at least partially within the primary stimulation current flow path I has been found to be unsatisfactory, because the substantial EMS currents produce artifacts in the EMG as shown in FIGS. 4A and 6B wherein an EMG artifact is induced into the raw EMG signal following each EMS pulse applied to the skin of the subject. We have further found that whereas voluntary attempts at muscular contraction in the presence of EMS produce a valid EMG signal when EMG measurement and EMS are effected using a common set of electrodes, the magnitude of the EMG is greatly attenuated and becomes even more highly attenuated with higher levels of electrical stimulation. This is probably due to the physiological refractory period following the hyperpolarization of excitable tissue by the stimulus pulse.

Figure 2:
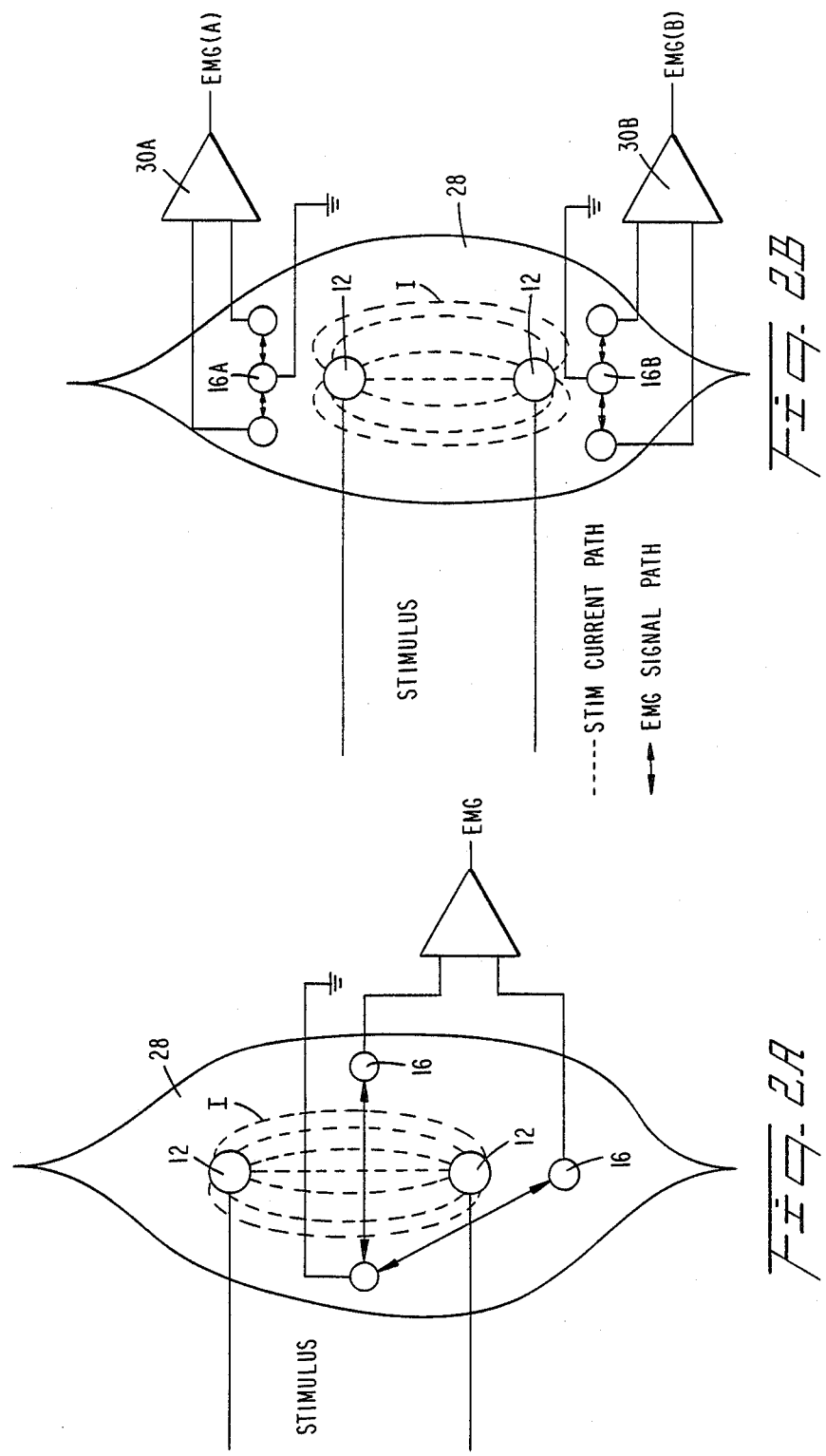
FIG. 2A is a diagram of a muscle site undergoing EMG measurement in the presence of EMS current, wherein the EMG electrodes are undesirably positioned in the primary stimulation current path.
FIG. 2B corresponds to FIG. 2A, with the EMG electrodes positioned properly outside the primary stimulation current path, in accordance with the invention.

Referring to FIG. 2B, proper positioning of EMG electrodes 16 and EMS electrodes 12 is shown. Therein, placement of the EMS and EMG electrodes 12, 16 is a very close approximation to common site stimulation and detection. However, the two different pairs of EMG electrodes 16A and 16B shown in the Figure are positioned on muscle site 28 just outside the primary current stimulation path I, whereby the EMG at the output of each buffer 30A, 30B is relatively free from EMG artifacts created by muscle stimulation current. However, even for EMG detection and electrical muscle stimulation sites that are relatively remote from each other, some electrical stimulus will tend to "spill over" into the detected EMG signal. This effect is removed in accordance with the invention by time-multiplexing and bandpass filtering, to be described hereinbelow.

Thus, referring to the simplified block diagram of FIG. 3 and associated waveforms of FIGS. 4A and 4B, the EMG signal conducted by electrodes 12 is amplified by amplifier 32, applied to a bandpass filter 34, then to a data acquisition interface 36. The amplifier 32 is a differential amplifier which amplifies by a predetermined gain the EMG differential signal at the two EMG electrodes 12. This EMG signal corresponds to EMG (A) or EMG (B) or a combination of the two in FIG. 2B. The bandpass filter, which has a high Q pass band from 1 kHz to 1 kHz, compresses the stimulus artifact into narrow time domain bursts, as shown in FIG. 4A, which can be suppressed by multiplexing in processor 38 to develop the pulses shown in FIG. 4B. The pulses of FIG. 4B are proportional in amplitude to the average value of the EMG during a time interval immediately preceding each pulse. The proportional response pulses are then current amplified in amplifier 40 to be applied as electrical stimulation signals to the muscle at output electrodes 16. The functional relationship between the processed EMG signal and generated EMS may be linear, although other relationships may be more appropriate in specific therapeutic applications.

With reference now to FIG. 4A in more detail, the EMG measured in the presence of electrical stimulation pulses comprises a first portion a which is an artifact consisting of a peak C created by the electrical muscle stimulation pulse applied to the muscle site and a decaying artifact component that follows. Thereafter, a portion b of the EMG, which is free to the artifact, is a raw EMG signal that is neurologically developed by the subject and is not related directly to the periodically applied EMS signal. It is this portion b of the EMG that is processed by signal processor 38 to develop an output pulse, such as pulse $c_1$ in FIG. 4B to be applied as an electrical muscle stimulation signal (EMS) to the muscle site.

Thus, assume that pulse $c_1$ in FIG. 4B is developed as a result of the raw EMG signal in FIG. 4A immediately preceding in time the generation of $C_1$. The pulse $c_1$ in FIG. 4B is amplified by power amplifier 40 in FIG. 3 to impart to the muscle site an electrical stimulation signal having an amplitude that corresponds specifically to the amplitude of pulse $c_1$. This pulse applied to the muscle site is measured at electrodes 12 as an EMG artifact, as shown at $C_1$ in FIG. 4A. Immediately thereafter, the artifact $C_1$ decays until what remains is the raw EMG in region b of FIG. 4A. The EMG at region b is processed in signal processor 38 by envelope detection and averaging, as described in detail herein below, to develop a second pulse $c_2$ in FIG. 4B. The pulse $c_2$ is again amplified by amplifier 40 to develop a second EMS pulse to be applied to the muscle site. This pulse is detected by EMG electrodes 16 as another artifact $C_2$ which, together with its decaying trailing portion a, is "masked" to enable the following raw EMG to be again processed to obtain the third EMS drive pulse $c_3$, and so on. Accordingly, the subject effectively controls his own EMS using EMS as a feedback component in neuromuscular re-education.

FIG. 5 is a circuit diagram of a more detailed implementation of proportional response EMS generation in accordance with the invention, with envelope detection to enhance sampling, and electrical isolation from the subject of processing circuitry. Amplifier 32 is again a differential amplifier having a gain sufficient to amplify the raw EMG signal detected by electrodes 12 to a usable level. The output of amplifier 32 is coupled, through an optocoupler 48, to a programmable gain amplifier 32a that enables the subject or attending personnel to control the gain of the EMG signal to be applied for processing to microprocessor 42.

The output of amplifier 32a is applied through a 1 kHz to 1 kHz bandpass filter 50 to an envelope detector 52 that converts the composite EMG and EMG artifact signal shown in FIG. 6A to an envelope shown in FIG. 6B having a magnitude that tracks the peak value of the composite EMG. This envelope is in turn applied, through an analog to digital converter 54, to microprocessor 42 programmed to sample [see FIG. 6(C)] the composite EMG only during the time period of each cycle when the EMG artifact has decayed to substantially zero. Microprocessor 42 samples the envelope waveform of FIG. 6B and, in response, develops digital data having values corresponding to the magnitude of the envelope of FIG. 6B, averaged over each period t as shown in FIG. 6C. Digital to analog converter 56 converts each digital value to the corresponding analog pulse, as shown in FIG. 6D, to be applied to amplifier 40 that drives the EMS electrodes 12 through an isolating pulse transformer 58. Programming of microprocessor 42 being known to one of ordinary skill in the art is omitted herein for brevity.

There has thus been described a method of and system for developing EMS signals that are a function of measured EMG, to be applied to stimulate muscles in neuromuscular re-education. Although specific circuitry for implementing proportional response EMS generation is described hereinabove, it is to be understood that other circuitry could alternatively be provided to perform the same functions. For example, for microprocessor based proportional response EMS generation, envelope detection can be realized either in hardware or in software, with the "dead-time" correction corresponding in time to the EMG artifact, performed in either hardware or software. Also although the EMS pulse train, pulse amplitude and pulse width developed by microprocessor 42 are all issued in real time via D/A converter 56, the converter may issue stimulus scale values and allow a timer/multiplexer network to generate the pulse train as a function of programmed pulse widths and pulse rates. Although no particular functional relationship between EMS and EMG magnitudes has been described in detail above, a linear relationship is preferred, although it is to be understood that other functional relationships tailored to particular individuals or developed during experimentation may be used within the spirit of this invention.

In addition, it is apparent that the invention described herein is applicable as a potential technique of "muscle amplification" whereby the strength of particular muscle sites is increased beyond that of which it ordinarily is capable in resonse to neurological signals developed by the subject.

In this disclosure, there is shown and described only the preferred embodiments of the invention, but, as aforementioned, it is to be understood that the invention is capable of use in various other combinations and environments and is capable of changes or modifications within the scope of the inventive concept as expressed herein.

We claim:

1. A bioelectrically controlled method of generating electrical muscle stimulation (EMS) signals, comprising the steps of applying to muscles to be stimulated an EMS signal having a particular magnitude; then after a time delay having a duration sufficient to enable EMG artifacts to decay, measuring volitionally produced electromyographic (EMG) signals developed by the muscles to be stimulated; processing the measured signals to obtain processed volitionally produced EMG signals and applying to the muscles an EMS signal having a magnitude that is related to said processed volitionally produced EMG signals.

2. A method as recited in claim 1, wherein said EMG measurements are made outside a primary stimulation current path of the applied EMS signal.

3. A method as recited in claim 1, wherein said step of measuring EMG signals includes applying a first pair of measurement electrodes to the skin of a subject near a muscle site to be electrically stimulated, and the steps of applying an EMS signal includes applying to the skin a second pair of stimulation electrodes, the first pair of electrodes being positioned outside a primary stimulation current path of the second pair of electrodes.

4. A method as recited in claim 1, wherein said signal processing step includes envelope detecting the measured volitionally produced EMG signals and said steps of applying EMS signals comprises applying variable amplitude, constant repetition rate pulses.

5. The method as defined in claim 1, wherein the applied EMS signals have magnitudes that are linearly proportional to said processed EMG signals.

6. The method of claim 1, wherein said processing step comprises averaging said measured volitionally produced EMG signals for a predetermined period of time.

7. An apparatus for generating bioelectrically controlled electrical muscle stimulation (EMS) signals, comprising:
   first electrodes to be applied to the skin of a patient near muscles to be stimulated;
   second electrodes to be applied to the skin of the patient for making electromyographic (EMG) measurements;
   means coupled to said second electrodes for developing EMG measurement signals including means synchronized to said EMS signals for sampling for said EMG measurement signals following decay of EMG artifacts;
   means for processing said sampled EMG measurement signals to produce processed EMG signals; and
   means coupled to said second electrodes electrical muscle stimulation (EMS) signal having a variable amplitude that is functionally related to said processed EMG signals.

8. An apparatus as recited in claim 7, wherein said EMG measurement signal processing means includes an envelope detector means for detecting an envelope of said EMG measurement signals.

9. An apparatus as recited in claim 7, wherein said sampling means includes multiplexing means synchronized to said EMS signal applying means for sampling said EMG signals.

10. An apparatus as recited in claim 7, wherein said sampling means includes a microprocessor.

11. The apparatus as defined in claim 7, wherein the EMS signals applied to said first electrodes have magnitudes that are linearly proportional to said processed EMG signals.

12. The apparatus of claim 7, wherein said processing means includes means for averaging said sampled EMS signals for a predetermined period of time.

13. An apparatus for bioelectrically controlled neuromuscular re-education by electrical stimulation, comprising:
   first electrodes to be applied to the skin of a patient near muscles to be stimulated;
   first means coupled to said first electrodes for generating electrical muscle stimulation (EMS) signals;
   second electrodes to be applied to the skin of the patient for making electromyographic (EMG) measurements;
   second means coupled to said second electrodes for producing EMG measurement signals; and
   processor means synchronized to said EMS signals for sampling said EMG measurement signals following decay of EMG artifacts and in response controlling said first means to generate pulsed EMS signals having a variable amplitude that is functionally related to said EMG measurement signals.

14. The pulsed apparatus as defined in claim 13, wherein the EMS signals generated by said first means have magnitudes that are linearly proportional to said EMG measurement signals.

15. A bioelectrically controlled method of generating electrical muscle stimulation (EMS) signals, comprising the steps of applying to a first muscle group of a patient an EMS signal having a particular magnitude; then after a time delay having a duration sufficient to enable EMG artifacts to decay measuring volitionally produced electromyographic (EMG) signals developed by a second muscle group of a patient; processing the measured volitionally produced EMG signals to obtain processed EMG signals and applying to the first muscle group of the patient an EMS signal having a magnitude that is functionally related to said processed EMG signals.

16. The method of claim 15, wherein said processing step comprises averaging said measured volitionally produced EMG signals for a predetermined period of time.

* * * * *